United States Patent
Kaniusas et al.

(10) Patent No.: US 12,178,567 B2
(45) Date of Patent: Dec. 31, 2024

(54) MEDICAL ANALYSIS DEVICE FOR ASSESSING A PATIENT'S SUITABILITY FOR ANAESTHESIA

(71) Applicants: Technische Universität Wien, Vienna (AT); Medizinische Universität Wien, Vienna (AT)

(72) Inventors: Eugenijus Kaniusas, Vienna (AT); Klaus Ulrich Klein, Vienna (AT); Florian Thürk, Vienna (AT); Stefan Kampusch, Vienna (AT)

(73) Assignees: Technische Universität Wien, Vienna (AT); Medizinische Universität Wien, Vienna (AT)

( * ) Notice: Subject to any disclaimer, the term of this patent is extended or adjusted under 35 U.S.C. 154(b) by 743 days.

(21) Appl. No.: 16/972,846

(22) PCT Filed: Jun. 7, 2019

(86) PCT No.: PCT/EP2019/064955
§ 371 (c)(1),
(2) Date: Dec. 7, 2020

(87) PCT Pub. No.: WO2019/234224
PCT Pub. Date: Dec. 12, 2019

(65) Prior Publication Data
US 2021/0244312 A1    Aug. 12, 2021

(30) Foreign Application Priority Data
Jun. 8, 2018    (EP) ..................................... 18176770

(51) Int. Cl.
*A61B 5/08* (2006.01)
*A61B 5/00* (2006.01)
(Continued)

(52) U.S. Cl.
CPC ........ *A61B 5/0826* (2013.01); *A61B 5/02108* (2013.01); *A61B 5/02405* (2013.01);
(Continued)

(58) Field of Classification Search
CPC .............. A61B 5/0826; A61B 5/02108; A61B 5/02405; G16H 50/20; G16H 50/30
See application file for complete search history.

(56) References Cited

U.S. PATENT DOCUMENTS

2018/0317859 A1*  11/2018  Kohli ................. A61B 5/02141

OTHER PUBLICATIONS

Choate, J. K., Denton, K. M., Evans, R. G., & Hodgson, Y. (2014). Using stimulation of the diving reflex in humans to teach Integrative Physiology. Advances in Physiology Education, 38(4), 355-365. https://doi.org/10.1152/advan.00125.2013 (Year: 2013).*

(Continued)

*Primary Examiner* — Paula J Stice
(74) *Attorney, Agent, or Firm* — Eversheds Sutherland (US) LLP

(57) ABSTRACT

The invention relates to a medical analysis device (1) for assessing a patient's suitability for anaesthesia by analysing at least one physiological biosignal (S) detected during an apnoea, wherein the medical analysis device (1) comprises the following: —an input interface (2) for detecting a time curve of at least one physiological biosignal (S) of a patient, —a computing unit (3) which is configured to compare a time curve of the at least one physiological biosignal (S) with at least one predefinable curve or a limit value according to an algorithm (4) in order to determine a patient's suitability for anaesthesia and to calculate an assessment result (E) depending thereon, wherein the time curve of the at least one physiological biosignal (S) comprises at least the duration of a patient's apnoea, and —an output interface (5) connected to the computing unit (3), to output the assessment result.

15 Claims, 4 Drawing Sheets

Figure 1:
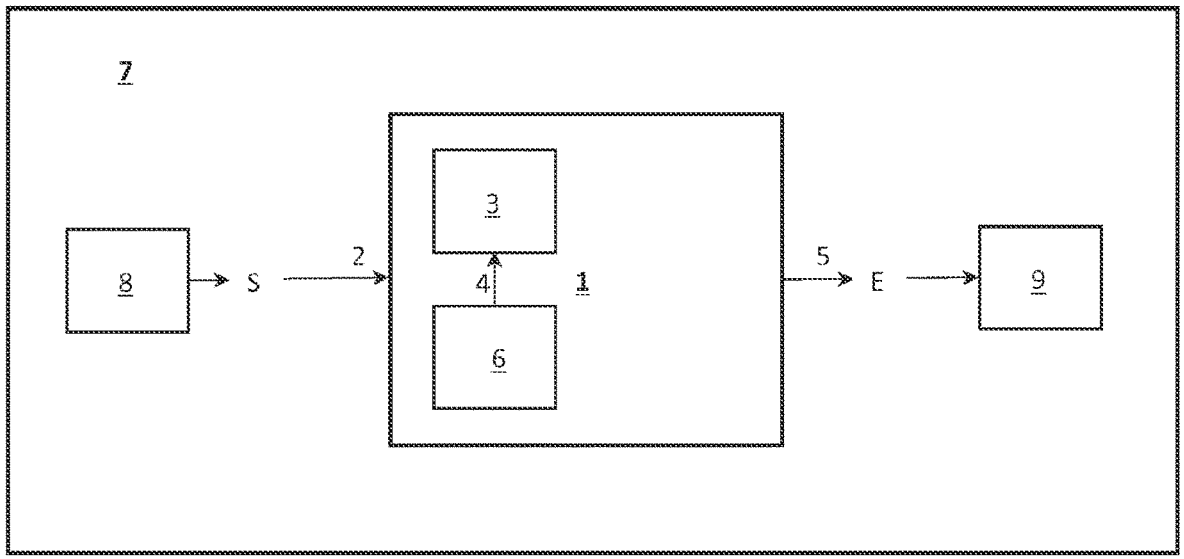

(51) Int. Cl.
- A61B 5/021 (2006.01)
- A61B 5/024 (2006.01)
- G16H 50/20 (2018.01)
- G16H 50/30 (2018.01)

(52) U.S. Cl.
CPC ............ *A61B 5/7292* (2013.01); *A61B 5/742* (2013.01); *A61B 5/7475* (2013.01); *G16H 50/20* (2018.01); *G16H 50/30* (2018.01)

(56) References Cited

OTHER PUBLICATIONS

Karnath, B. M. (2002). Preoperative considerations and risk assessment. Manual of Perioperative Care in Adult Cardiac Surgery, 91-127. https://doi.org/10.1002/9781444318364.ch3 (Year: 2002).*

Vincenzi, F. F. (2019). Sudden unexpected death and the mammalian dive response: Catastrophic failure of a complex tightly coupled system. Frontiers in Physiology, 10. https://doi.org/10.3389/fphys.2019.00097 (Year: 2019).*

International Search Report for International Application No. PCT/EP2019/064955, dated Aug. 28, 2019. (2 pages).

European Search Report for Application No. EP18176770, dated Oct. 23, 2018. (1 page).

Rigg, J.R.A., et al., "Clinical Assessment of Respiratory Function", British Journal of Anaesthesia, vol. 50, No. 1, Jan. 1, 1978. (12 pages).

Struthers, R., et al., "Assessing Fitness for Surgery: A Comparison of Questionnaire, Incremental Shuttle Walk, and Cardiopulmonary Exercise Testing in General Surgical Patients", British Journal of Anaesthesia, vol. 101, No. 6, Dec. 1, 2008. (8 pages).

Kaniusas, E., et al., "Angehaltene Atmung Aus Physiologischer Sicht: Theorie, Experiment Und Forschung", Caisson, vol. 31, Apr. 1, 2016. (68 pages).

* cited by examiner

MEDICAL ANALYSIS DEVICE FOR ASSESSING A PATIENT'S SUITABILITY FOR ANAESTHESIA

The invention relates to a medical analysis device for assessing a patient's suitability for anaesthesia.

The routine assessment of fitness for anaesthesia or suitability for anaesthesia within the scope of a health examination is based on the preoperative collection of the patient's clinical history, and the stress threshold as subjectively perceived by the patient, and their individual fitness (for example physical comfort when climbing stairs) within the scope of the medical history, followed by clinical assessment and evaluation (for example assessment of anatomy and pathology).

For a more precise clarification of fitness for anaesthesia, additional physical examinations are carried out as required—if risk factors exist or at an advanced age and taking into account national and international guidelines and recommendations—such as a (stress) electrocardiogram (ECG), an X-ray thorax examination, routine blood tests or, more rarely, a heart ultrasound or orthostatic test. The latter test is used to detect autonomic dysfunction and associated inadequate compensatory vasoconstriction of the cardiovascular system, which can make anaesthesia considerably more difficult during an operation. In addition, if necessary, laboratory chemical biomarkers are tested (for example pro-BNP, troponin), which allow a risk assessment of the cardiovascular system. Of particular importance, however, is the status of the autonomic nervous system, the deterioration of which in the perioperative setting (before, during and after the operation) can lead to undesirable cardiovascular events (for example difficult anaesthetic delivery in the sense of a drop or rise in blood pressure, the need to administer circulatory support drugs during or after the operation, intermittent atrial fibrillation or other cardiac arrhythmias, stroke, heart failure or heart attack during or after the operation).

Based on the estimated individual fitness for anaesthesia, for example proceeding from the standardised ASA classification (classification of the American Society of Anesthesiologists, with I for a healthy patient to VI for a brain dead patient, or another more specific classification), the anaesthetist can prepare for the upcoming perioperative challenges that anaesthesia brings (analgesia, hypnosis, amnesia, muscle relaxation and respiratory suppression). In particular, the expected pathological deviations in body homeostasis in the operating theatre can be better predicted and more efficiently compensated for, for example various stress situations in the body's circulatory system can/must be compensated for by the anaesthetist by means of the administration of volume and/or circulatory support drugs. A successful prediction of the physiological state in the perioperative setting is therefore of vital importance for the choice and implementation of the anaesthetic method, for its effectiveness, for the avoidance of cardiovascular and other complications, and thus for a successful complication-free outcome and as a guarantee for the best-possible recovery of the patient. In particular, the way in which anaesthesia is carried out in high-risk patients, such as those undergoing major abdominal, orthopaedic, trauma, gynaecological or urological surgery, as well as in cardiac, thoracic and vascular surgery, depends on an accurate assessment of the patient's fitness for anaesthesia.

A subjective static assessment of fitness for anaesthesia (for example static resting heart rate and stationary heart rhythm, static resting blood pressure and haemoglobin-oxygen saturation under ambient air) is possible and is regularly carried out before operations, while objective physical dynamic examinations are rarely carried out due to time and cost reasons, typically only in the case of special high-risk patients and operations, often with a high equipment outlay. Physical examinations (orthostatic test to test the autonomic nervous system, stress electrocardiography or echocardiography) also require patients to be mobile (for example bedridden or severely physically restricted or very ill patients must be excluded), which is why these examinations are rarely carried out in clinical practice, and why new methods for determining suitability for anaesthesia must be developed.

The above-mentioned possibilities for detecting fitness for anaesthesia either require mobility of the patient or only provide rough subjective static estimates of fitness for anaesthesia.

It is therefore the object of the present invention to create a device by means of which the detection of the fitness for anaesthesia is reliably permitted or improved and which simplifies execution of this process.

This object is achieved in accordance with the invention with a medical analysis device for assessing a patient's suitability for anaesthesia by analysing at least one physiological biosignal detected during an apnoea (a deliberate holding of breath), wherein the medical analysis device comprises the following:

an input interface for detecting a time curve of at least one physiological biosignal of a patient, a computing unit which is configured to compare a time curve of the at least one physiological biosignal with at least one predefinable curve or a limit value according to an algorithm in order to determine a patient's suitability for anaesthesia and to calculate an assessment result depending thereon, wherein the time curve of the at least one physiological biosignal comprises at least the duration of a patient's apnoea, and an output interface connected to the computing unit, to output the assessment result, wherein at least one of the following physiological biosignals is detected and is processed in the algorithm: {arterial oxygen saturation, arterio-venous oxygen saturation, peripheral pulse wave (for example at the finger), central pulse wave (for example at the earlobe), respiratory activity, ECG data, heart rate variability, arterial blood pressure}.

The two pulse waves mentioned can be recorded optically (for example via oximeter), mechanically (for example skin curvature sensor) and electrically (for example electrical plethysmography).

In principle, a single biosignal may be sufficient, which is derived from an electrocardiogram and/or the arterial blood pressure (recorded by a non-invasive blood pressure monitor) and/or the arterial pulse waveguide velocity and/or the peripheral haemoglobin oxygen saturation can be measured. Oxygen saturation can be particularly significant and is suitable as a criterion.

In contrast to the prior art, this allows a simple, objective, reproducible, non-invasive, methodologically clear and physiologically determined assessment of the momentary fitness for anaesthesia in all patients (regardless of whether or not they are mobile). The invention detects the dynamic functional fitness for anaesthesia, wherein this—based in methodological terms on the dynamic changes to be expected during anaesthesia—can be used in the future instead of static anatomical or structural fitness for assessing the fitness for anaesthesia and provides a more reliable assertion of the actual fitness for anaesthesia of a patient.

The assessment of the fitness for anaesthesia should be carried out during the pre-anaesthesia consultation (pre-medication) and should be of short duration only, in order to provide the anaesthetist with a quick aid in assessing the patient's suitability for anaesthesia.

The present invention also offers a practical and unique possibility to check the existing dynamic cardiovascular cardiorespiratory and cerebrovascular reserve capacity and thus the functional fitness for anaesthesia of patients who, for various reasons, are bedridden, reduced in performance or drive, up to states of drug-induced or other unconsciousness and possibly machine ventilation. The necessary apnoea phase can also be adjusted via the ventilator in mechanically ventilated patients if required.

In particular, the algorithm may be designed to automatically detect the onset of apnoea and the end of apnoea by analysing the change over time of at least one physiological biosignal. For example, the onset of apnoea may be deduced from an ECG by at least two methods:
  (i) as the heart axis spatially oscillates synchronously with breathing, the ECG amplitude also oscillates over the respiratory cycle; stopped breathing suppresses this oscillation,
  (ii) the RR interval from ECG oscillates up and down during inspiration and expiration; stopped breathing suppresses this oscillation (this oscillation tends to decrease with the severity of the disease).

Both methods (i) and (ii) can also be combined/applied simultaneously to increase the robustness of apnoea detection.

Advantageously, it may be provided that physiological biosignals recorded at least for a period of 180 seconds (preferably three to five minutes) before the onset of apnoea are taken into account in the calculation of the assessment result. Preferably, the corresponding physiological biosignals are continuously recorded and stored for a pre-defined period of time. It may also be provided that physiological biosignals recorded for at least 180 seconds (preferably three to five minutes) after the end of apnoea are taken into account in the calculation of the assessment result. The medical analysis device may therefore have a memory designed to store the corresponding biosignals for a period of at least 420 seconds (for example 180 seconds before the apnoea, 60 seconds duration of apnoea and 180 seconds after the end of the apnoea). For example, the apnoea can last between 10 and 90 seconds, preferably between 30 and 60 seconds.

In particular, provision may be made for at least one of the following physiological biosignals to be recorded and processed in the algorithm {peripheral arterial haemoglobin-oxygen saturation ($SpO_2$), for example by means of an oximeter attached to a finger of the patient, peripheral pulse wave, pulse waveguide velocity, ECG data, heart rate variability, arterial blood pressure as well as blood pressure variability (all parameters for the evaluation of the cardiovascular system and cardiovascular reserve capacity)}.

It has proved to be particularly suitable for practical use if at least one biosignal of the following group is selected and the biosignal in question is assigned a limit value that lies within the range specified below: {$SpO_2$ with limit value 94-100%, systolic blood pressure (RRsys) with limit value 90-120 mmHg, diastolic blood pressure (RRdia) with 60-80 mmHg (according to American Heart Association guidelines), heart rate (HR) with 60-100/min}.

In particular, provision may be made for at least two or more biosignals to be detected and taken into account to calculate the assessment result. Correspondingly consistent agreement of the temporal changes in the biosignals can, for example, increase the accuracy of the assertion regarding the fitness for anaesthesia.

In addition, it may be provided that the medical analysis device is designed to capture patient-specific data, in particular age, height and weight, body mass index (BMI) and/or previous cardiovascular or respiratory illnesses of the patient, for example by means of an input interface or the input interface, wherein the algorithm takes the captured patient-specific data into account when calculating the determination of the patient's suitability for anaesthesia. In this way, expected values can be created with regard to absolute values as well as temporal changes in the values of the biosignals, which can be taken into account in the calculation of the fitness for anaesthesia as well as in the selection of limit values.

In particular, it may be provided that the computing unit is assigned a storage medium on which the algorithm for determining the fitness for anaesthesia of a patient is stored. The medical analysis device is thus already sufficiently prepared for use and only needs to be supplied with appropriate biosignals for its application.

It may also be provided that the output interface is a digital or analogue interface for connecting an external output device, in particular a visual display and/or an acoustic display.

Alternatively, it may be provided that the output interface is a digital or analogue interface for connecting an output device, in particular a visual display and/or an acoustic display, wherein the medical analysis device comprises the output device.

The display can be in the form, for example, of an optical traffic light system or a multi-step, for example five-step, scale.

The invention also relates to a system comprising a medical analysis device according to the invention and at least one sensor for detecting a physiological biosignal of a patient, wherein the at least one biosignal is selected from the following group: {peripheral arterial oxygen saturation; peripheral pulse wave, pulse waveguide velocity, ECG data, heart rate variability, arterial blood pressure and its variability}. It may also be provided that the system comprises at least two or more sensors that detect at least two or more of the aforementioned biosignals. For example, one sensor may be provided for each biosignal. In particular, a plurality of sensors may also be provided to measure all of the aforementioned biosignals. It may also be that one sensor is provided for measuring a plurality of biosignals (multiparametric sensor).

The sensors may include, for example, a respiratory belt placed around the thorax for more accurate detection of apnoea duration (especially if ECG is of poor quality and therefore the methods (i) and (ii) described for detecting the onset and end of apnoea fail), as well as sensors for measuring pulse waveguide velocity and blood pressure variability.

It may also be provided that the system comprises an output device which is connected to the output interface of the medical analysis device and which in particular comprises a visual display and/or an acoustic display.

The invention further relates to a storage medium on which an algorithm according to the invention for measuring fitness for anaesthesia is stored.

The medical analysis device allows the determination of an objective functional standardisable suitability for anaesthesia on the basis of dynamic physiological non-invasive biosignals, wherein, for example, the peripheral arterial oxygen saturation, the peripheral pulse wave, the pulse waveguide velocity, and/or the heart rate and blood pressure variability can be used as biosignals, these being recorded before, during and after the deliberate holding of breath.

The medical analysis device is designed for use by doctors, in particular anaesthetists, to assess the suitability for anaesthesia within the context of the preoperative health examination.

The respiratory manoeuvre of deliberate holding of breath necessarily causes an imbalance in various physiological parameters, as the supply of oxygen is interrupted, as is the exhalation of carbon dioxide. This imbalance represents a mild stress situation for the human body, is not a stationary state, and can only be maintained temporarily. In order to tolerate and compensate for this state, various stress-relieving actions are initiated in the body—commonly known as the diving reflex, mediated by the vagus nerve. These actions are mediated by increased parasympathetic tone and include, among other things, a lowered heart rate to reduce oxygen consumption in the heart and reduced blood flow to the extremities to reduce oxygen consumption peripherally.

The temporal course as well as the strength of these compensatory actions during apnoea are strongly dependent on the presence and expression of regulatory phenomena in the cardiovascular, cardiorespiratory and cerebrovascular systems of the human body. From a physiological point of view, apnoea is a dynamic breathing manoeuvre and not a static state, which triggers a dynamic response reaction of the body. The invention makes use of the fact that this dynamic response reflects not only static anatomical structural concerns, but also the functional haemodynamic state. These regulatory phenomena in turn describe the adaptability of the internal systems to the given circumstances, i.e. to the apnoea, which can also be understood as cardiovascular, cardiorespiratory and cerebrovascular fitness.

Therefore, a signalling recording of the compensatory actions by means of the medical analysis device before, during and after the apnoea can be used to assess the efficiency of the intrinsically dynamic control circuits in the body and therefore also to assess the resulting cardiovascular, cardiorespiratory and cerebrovascular fitness. The more dominant the compensatory actions are—for example in the sense of a pronounced diving reflex—the higher is said fitness.

This cardiovascular, cardiorespiratory and cerebrovascular fitness derived from the apnoea is now comparable to the fitness for anaesthesia, since the perioperative stress situations also represent an individual temporary imbalance for the cardiovascular, cardiorespiratory and cerebrovascular system. In particular, voluntary apnoea reflects the cardiovascular, cardiorespiratory and cerebrovascular reserve that is demonstrably and measurably utilised during apnoea. A similar reserve is also called up and utilised in the perioperative setting. Not only the existing anatomical, but also the functional pathology of the patient is reflected and quantified by this reserve, which is essential for the planning of a safe and stable anaesthesia. In addition, during apnoea a blood volume is shifted/centralised, while a change in volume (for example bleeding during surgery) and its functional influence plays a major role in the perioperative area. Cardiovascular, cardiorespiratory and cerebrovascular fitness also determines physiological/biological age, which is an essential parameter of fitness for anaesthesia.

The chosen respiratory manoeuvre of voluntary apnoea is similar to the involuntary apnoea during anaesthetic induction. This involuntary apnoea occurs during the time when various accesses to the lungs are placed in position for artificial respiration and can last several minutes until the activation of artificial respiration under reduced patient monitoring. Therefore, the preoperatively monitored voluntary apnoea during the health examination can provide helpful physiological information about the less monitored involuntary apnoea during the anaesthetic induction in the operating theatre. In voluntary and involuntary apnoea, the arterial blood becomes less oxygenated, so that voluntary apnoea can be used to estimate the expected desaturation of the blood during the induction of anaesthesia. Furthermore, the selected vital biosignals in voluntary apnoea are also those to which the anaesthetist attaches particular importance and attention in the operating theatre.

From an application point of view, the breath is deliberately held on command, so that the apnoea is also deliberately terminated. This prevents any possible damage caused by the voluntary respiratory manoeuvre. The mobility of the patient is not a prerequisite, so that bedridden patients can also perform the breath-holding manoeuvre. The patient can therefore be examined sitting, lying or standing. A cooperative behaviour of an awake patient is required. If the artificial respiration is stopped for a short time (for example for 2-3 breaths), a defined protocol is then performed to immediately compensate for the resulting ventilation gap. As mentioned above, the apnoea manoeuvre can also be performed in principle on mechanically ventilated patients by adjusting the ventilation (ventilator).

No drugs or gases with side effects are used to achieve the physiological imbalance. The reproducibility of the apnoea-based results is high and apnoea is well tolerated by patients.

The monitoring results of suitability for anaesthesia can be presented in a generally understandable form of a scale ranging from one to five, so that the anaesthetist can immediately interpret and use the measured suitability for anaesthesia.

An objective assessment of suitability for anaesthesia offers maximum chances of taking preventive measures, in advance of the upcoming extreme body conditions in the operating theatre.

Various markers are derived from the measured biosignals, such as arterial oxygen saturation, peripheral pulse wave, heart rate variability and arterial blood pressure before, during and after voluntary stopped breathing. These parameters could not be routinely determined preoperatively before now and provide important information for the functional resilience of the cardiovascular system and the expected stability of anaesthesia delivery. The following parameters, for example, are possible markers:

sympathetic tone of the patient, as a marker of the body's responsiveness to the administration of drugs and volume reduction and loading in the operating theatre;

sympathovagal tone of the patient, as a marker for the current state of the vegetative (autonomic) nervous system (for example marker for the resilience of the cardiovascular system), which deteriorates during anaesthesia in the sense of an imbalance (sympathetic>parasympathetic). The reserve of this tone existing before the operation is therefore recorded;

hypoxia-induced respiratory urgency, as a marker of the possible presence of autonomic neuropathy (reduced respiratory urgency), essential for stable anaesthesia delivery;

arterial baroreflex, as a marker of the autonomic nervous system, abnormal values of which lead to risks (for example abnormal drop and rise in blood pressure and heart rate) during anaesthesia;

respiratory sinus arrhythmia, as a marker for the current state of the vegetative (autonomic) nervous system.

Figure 2:
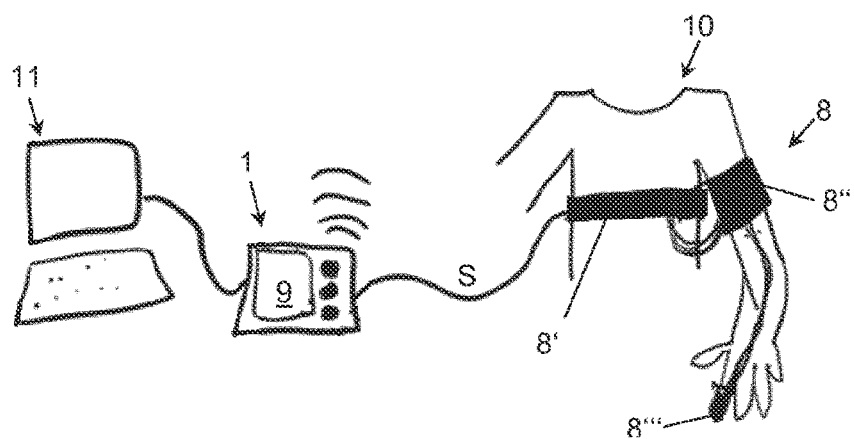

The invention is explained in more detail in the following on the basis of exemplary and non-limiting embodiments, which are illustrated in the figures, in which FIG. 1 is a schematic representation of a medical analysis device according to the invention, FIG. 2 is a schematic representation of a system according to the invention during use, and FIGS. 3 to 6 are exemplary embodiments of algorithms for the assessment of a patient's suitability and fitness for anaesthesia.

In the following figures—unless otherwise indicated—the same reference signs denote the same features.

FIG. 1 shows a schematic representation of a medical analysis device 1 according to the invention within a system 7 comprising the medical analysis device 1. The medical analysis device 1 is designed to assess the suitability for anaesthesia of a patient 10 (see FIG. 2), more specifically by analysing at least one physiological biosignal S detected during the period of apnoea, the medical analysis device 1 comprising the following:

an input interface 2 for detecting a time curve of at least one physiological biosignal S of a patient 10, a computing unit 3 which is configured to compare a time curve of the at least one physiological biosignal S with at least one predefinable curve or a limit value according to an algorithm 4 in order to determine the suitability of a patient 10 for anaesthesia and to calculate an assessment result E depending thereon. Here, the time curve of the at least one physiological biosignal S is detected at least for the duration of apnoea of the patient 10, and an output interface 5 connected to the computing unit 3, to output the assessment result.

The computing unit 3 is assigned a storage medium 6, on which the algorithm 4 for determining the suitability for anaesthesia of a patient 10 is stored. This storage medium 6 can also be used to store the data regarding the detected biosignals S. The analysis device 1 can also comprise sensors 8 for measuring the biosignals S, or can be connected to external sensors 8 via the input 2.

For example, the sensors 8 can detect the following physiological biosignals S, which are processed according to the algorithm 4: {arterial oxygen saturation; peripheral pulse wave, ECG data, heart rate variability, arterial blood pressure}.

It may also be provided that at least two or more biosignals S are detected and taken into account for the calculation of the assessment result. Calculation examples for this are shown in FIGS. 3 and 4, which show exemplary versions of an algorithm 4 for calculating the suitability for anaesthesia of a patient 10.

FIG. 2 shows a schematic representation of a system 7 according to the invention in its application. The system 7 comprises the medical analysis device 1, wherein, in order to provide a better overview, the individual components of the analysis device 1 already mentioned in FIG. 1 are not shown in detail. Furthermore, the system 7 comprises at least one sensor 8 for detecting a physiological biosignal of a patient, wherein the at least one biosignal is selected from the following group: {peripheral arterial oxygen saturation; peripheral pulse wave, ECG data, heart rate variability, arterial blood pressure}. In the present case, a plurality of sensors are provided, such as a chest strap 8' with integrated electrodes for taking ECG measurements, an arm pressure cuff 8'' for measuring blood pressure, and, for example, an oximeter 8''' attached to a patient's finger for measuring oxygen saturation or for recording a photoplethysmogram (PPG).

A treating physician can obtain information on the assessment result in the form of a graphic representation (for example in the form of a traffic light system), a display and/or an acoustic output by means of an output device 9 arranged on the analysis device 1. External data such as patient-specific information (for example age, previous illnesses, etc.) can be entered, for example, via an external input device, in particular via a computer 11 including keyboard, or by means of medical equipment already available in a hospital and having an appropriate input surface.

Figure 3:
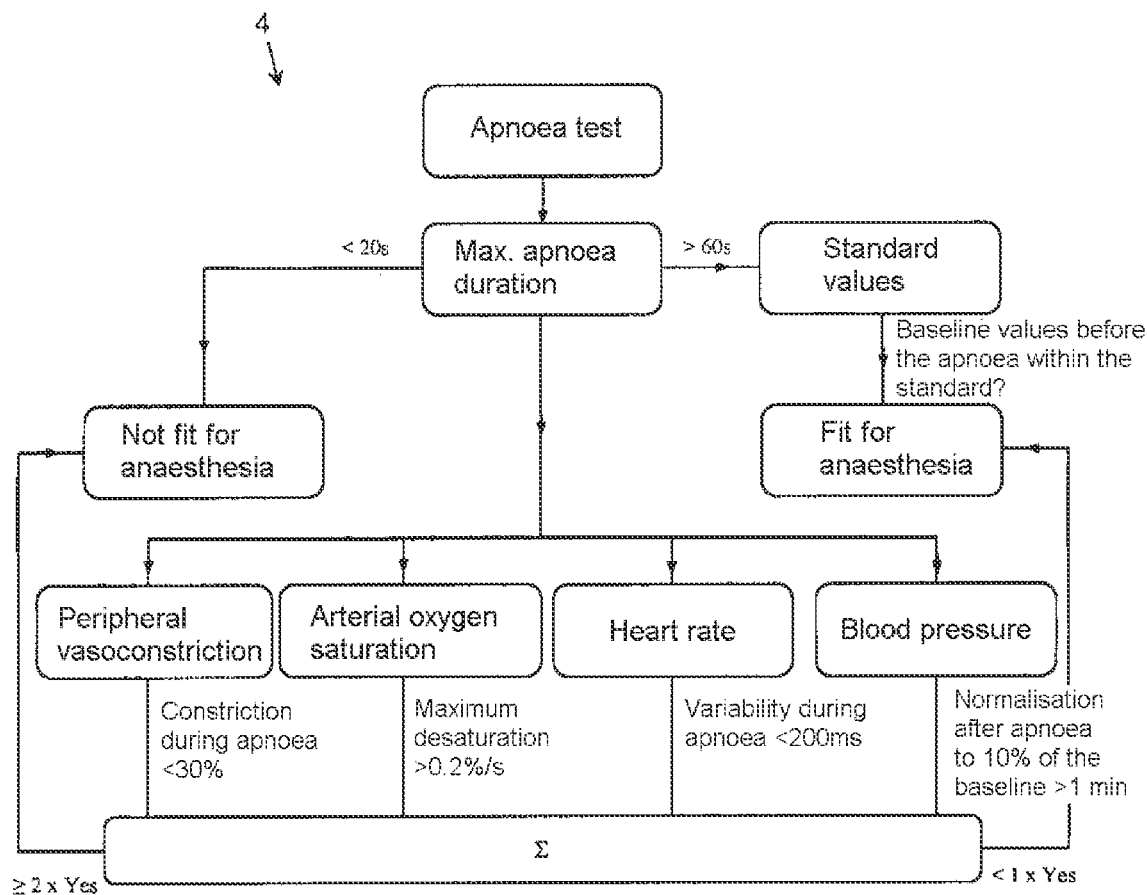
Figure 4:
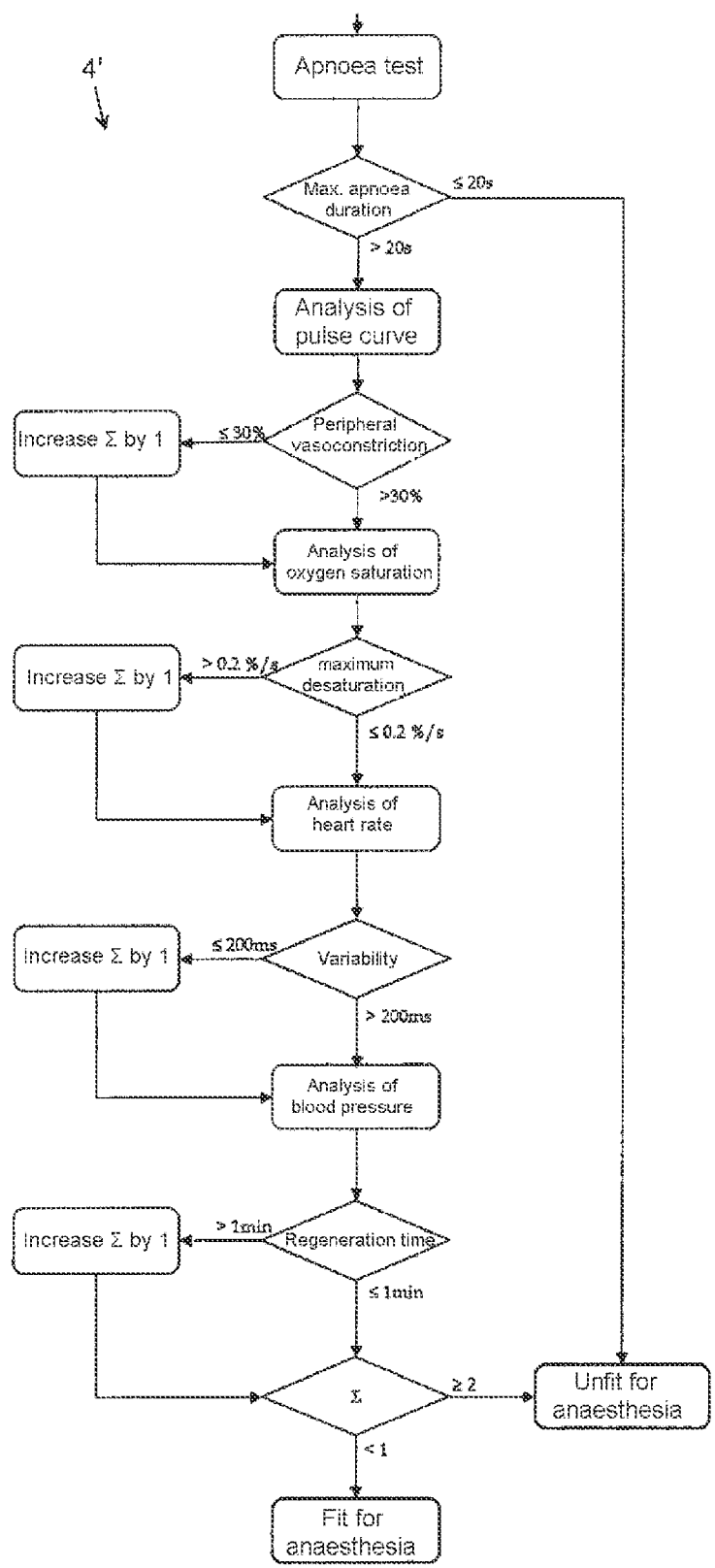

FIGS. 3 and 4 show exemplary embodiments of algorithms 4 in the form of flowcharts for the assessment of the suitability and fitness for anaesthesia of a patient 10.

The algorithm according to FIG. 3 distinguishes between three different durations of apnoea. If the patient 10 is not able to hold his breath voluntarily for at least 20 seconds, it is concluded that he is not fit for anaesthesia. If, on the other hand, the patient is able to hold his breath without restriction for a period of more than 60 seconds, it can be concluded that he is sufficiently fit for anaesthesia. If the duration is between 20 and 60 seconds, biosignals such as heart rate, blood pressure, peripheral vasoconstriction or arterial oxygen saturation are used to determine fitness for anaesthesia and are compared with reference values or reference runs. The sum of the available comparisons can then be compared with a sum limit value, wherein the absence or presence of fitness for anaesthesia can be concluded depending on the comparison. FIG. 3 gives examples of comparison and limit values. It goes without saying that these values are exemplary and can vary in individual cases, just as the specific design of the algorithm 4 can vary.

For example, FIG. 4 shows a further design of an algorithm 4', in which the maximum apnoea duration, peripheral vasoconstriction, maximum desaturation, heart rate variability, and regeneration time of the blood pressure are included in the calculation of fitness for anaesthesia.

Figure 5:
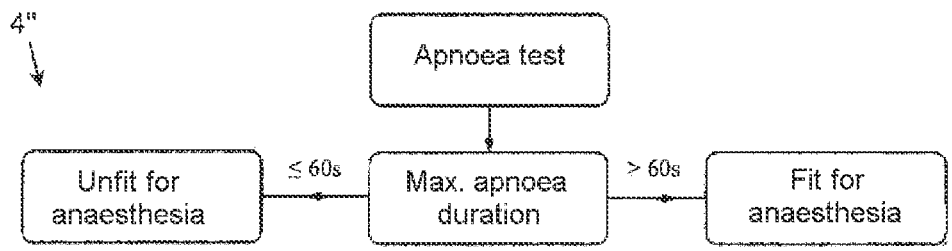

FIG. 5 shows another example of an algorithm 4'', which is a highly simplified embodiment of the algorithm in FIG. 3. Here, only the duration of apnoea is recorded. This simple test can be used as a preliminary criterion for the preliminary selection of patients with fitness for anaesthesia. If the patient holds his breath for more than 60 s (conservative criterion), he is fit for anaesthesia. If the patient can only hold his breath for a shorter period of time, the result is that the fitness for anaesthesia is questionable; further tests (for example according to one of the algorithms in FIG. 3, 4 or 6) must be carried out, or, if this is not possible, the patient is classified as not fit for anaesthesia.

Figure 6:
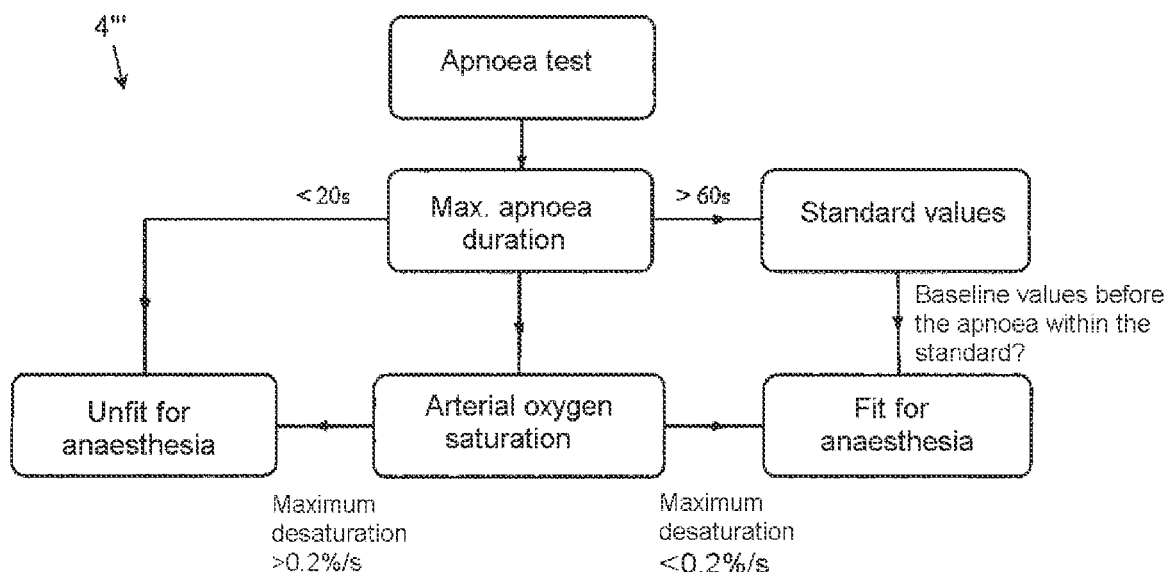

FIG. 6 shows another example of an algorithm 4''', in which, in addition to the duration of apnoea, arterial oxygen saturation is used, for example. If the duration of apnoea is less than 20 s, there is no fitness for anaesthesia (regardless of any desaturation observed). For over 60 s, fitness is inferred (also independently of oxygen saturation). For values of apnoea duration in between, the examined course of oxygen saturation is also used. For example, a value of 0.2%/s can be used as a criterion (in the product with the respective apnoea duration). If, for example, the apnoea duration is 30 s, the threshold of desaturation is 0.2*30=6%: If the determined desaturation exceeds the value 6%, for example because the oxygen saturation has dropped from 98% to 92%, there is a lack of fitness. If, on the other hand, desaturation is less than 6% during the apnoea period (for example because oxygen saturation has fallen from 98% to 95%), fitness is still present.

Below is a tabular list of exemplary criteria that are taken into account to determine fitness for anaesthesia (the result "healthy" indicates the presence of fitness for anaesthesia, the result "ill" indicates the absence of fitness for anaesthesia)

| Healthy versus ill | |
|---|---|
| Healthy (ASA I) | Ill (ASA > I) |
| Long maximum duration of voluntary apnoea (for example over 60 s) | Short maximum apnoea duration (approximately 40% reduction in relation to healthy population) |
| Strong and quick variability of the recorded cardiovascular parameters (for example heart rate and pulse wave amplitude) during the voluntary apnoea | Reduced and slow variability of the cardiovascular parameters |
| Pronounced respiratory sinus arrythmia - periodic fluctuation of the heart rate synchronously with respiration - before and after the apnoea | Weak respiratory sinus arrhythmia |
| Strong progressive peripheral vasoconstriction during the apnoea (diving reflex and/or stress response), identifiable from the progressive reduction of the fluctuation margin of the peripheral pulse wave (approximately 30-50% reduction in comparison to the baseline); strong temporary vasodilation after the apnoea (intensified circulation for compensation of the local oxygen deficit), identifiable from the increase in the fluctuation margin (approximately 50% increase in comparison to the baseline) | Weak to non-existent peripheral vasoconstriction during the apnoea, the fluctuation margin hardly changes over the apnoea duration; no significant vasodilation following the apnoea. |
| Weak correlation between rise in blood pressure and rise in heart rate (because peripheral resistance is also modulated during the apnoea) | Strong correlation between rise in blood pressure and rise in heart rate (no modulated of the peripheral resistance) |
| Strong desaturation during the apnoea (for example reduction at 10%); very heavily dependent on the apnoea duration | Weak desaturation during the apnoea (for example reduction at 7%) |
| Rapid normalisation of the reduced oxygen saturation after the apnoea | Slow normalisation of the reduced oxygen saturation after the apnoea (up to 2-3 minutes) |
| Low cumulative duration of desaturation | High cumulative duration of desaturation |
| Rapid normalisation of the increased blood pressure values after the apnoea, partially below the baseline (following vasodilation) | Slow normalisation of the increased blood pressure values after the apnoea (up to 2-3 minutes), no drop below the baseline |
| Low average blood pressure | High average blood pressure |
| Low average heart rate during the apnoea | High average heart rate during the apnoea |
| Large change in heart rate during the apnoea (large heart rate variability) | Low change in heart rate during the apnoea (ASA II - reduction at approximately 30% in comparison to ASA I, ASA III - reduction at approximately 70% compared to ASA I), reduction up to a factor of 4 to 5 |

In view of this teaching, a person skilled in the art is able to arrive at other embodiments (not shown) of the invention without exercising inventive skill. The invention is not limited to the shown embodiments. Individual aspects of the invention or the embodiment can also be selected and combined with each other. Essential are the ideas underlying the invention, which can be carried out by a person skilled in the art in the knowledge of this description in a variety of ways and still can be maintained as such. Any reference signs in the claims are exemplary and serve only to make the claims easier to read, without restricting them.

The invention claimed is:

1. A medical analysis device (1) for assessing suitability for anaesthesia of a patient by analysing at least one physiological biosignal (S), the medical analysis device (1) comprising:
  one or more sensors (8) for detecting physiological biosignals (S) of the patient, wherein the physiological biosignals (S) include at least two of: arterial oxygen saturation, respiratory activity, heart rate variability, peripheral vasoconstriction, or arterial blood pressure,
  a computing unit (3) which is configured to:
    determine that at least two of the physiological biosignals (S) indicate that the patient is unfit for anaesthesia, and
  an output device (9) connected to the computing unit (3), to output an indication that the patient is unfit for anaesthesia.

2. The medical analysis device (1) according to claim 1, wherein the computing unit (3) is further configured to automatically detect an onset of apnoea and an end of apnoea by analysing a change over time of the respiratory activity.

3. The medical analysis device (1) according to claim 1, wherein the physiological biosignals (S) are recorded at least for a period of 180 seconds before an onset of a period of apnoea for the patient.

4. The medical analysis device (1) according to claim 1, wherein the physiological biosignals (S) are recorded at least for a period of 180 seconds after an end of the period of apnoea for the patient.

5. The medical analysis device (1) according to claim 1, wherein the computing unit (3) is assigned a non-transitory storage medium (6).

6. The medical analysis device (1) according to claim 1, wherein the output device (9) is a visual display and/or an acoustic display.

7. A system (7) comprising the medical analysis device (1) according to claim 1 and further comprising sensors (8) for detecting the physiological biosignals (S) of the patient.

8. A non-transitory storage medium (6) on which an algorithm (4) according to the medical analysis device (1) of claim 1 is stored.

9. The medical analysis device (1) according to claim 1, wherein the computing unit (3) determines that at least two of the physiological biosignals (S) indicate that the patient is not suitable for anaesthesia based on at least two of:
  the arterial oxygen saturation is greater than a desaturation threshold,
  the heart rate variability is less than a variability threshold,
  the peripheral vasoconstriction is less than a constriction threshold, or
  the arterial blood pressure regenerates at a time longer than a threshold time.

10. The medical analysis device (1) according to claim 1, wherein the computing unit (3) is further configured to:

determine that the patient is unfit for anaesthesia based on at least two of the physiological biosignals (S) indicating that the patient is unfit for anaesthesia.

11. A method for assessing suitability for anaesthesia of a patient, the method comprising:
- detecting, with one or more sensors (8), physiological biosignals (S) of a patient, wherein the physiological biosignals (S) include at least two of: arterial oxygen saturation, respiratory activity, heart rate variability, peripheral vasoconstriction, or arterial blood pressure,
- determining, using a computing unit (3), that at least two of the physiological biosignals (S) indicate that the patient is unfit for anaesthesia, and
- outputting, using an output device (9), an indication that the patient is unfit for anaesthesia.

12. The method of claim 11, further comprising:
- automatically detecting, using the computing unit (3), an onset of apnoea and an end of apnoea by analysing a change over time of the respiratory activity.

13. The method of claim 11, wherein the physiological biosignals (S) are recorded at least for a period of 180 seconds before an onset of a period of apnoea for the patient.

14. The method of claim 11, wherein the physiological biosignals (S) are recorded at least for a period of 180 seconds after an end of the period of apnoea for the patient.

15. The method of claim 11, wherein determining that at least two of the physiological biosignals (S) indicate that the patient is not suitable for anaesthesia comprises at least two of:
- the arterial oxygen saturation is greater than a desaturation threshold,
- the heart rate variability is less than a variability threshold,
- the peripheral vasoconstriction is less than a constriction threshold, or
- the arterial blood pressure regenerates at a time longer than a threshold time.

* * * * *